(12) United States Patent
Schaller et al.

(10) Patent No.: US 9,279,038 B2
(45) Date of Patent: Mar. 8, 2016

(54) METHOD FOR PRODUCING CROSS-LINKED ELASTOMER

(75) Inventors: Raimund Schaller, Neunkirchen (AT); Armin Holzner, Ternitz (AT); Richard Ehrenfeldner, Ternitz (AT); Michael Hoechtl, Wien (AT); Wolfgang Kern, Seiersberg (AT); Franz Stelzer, Graz (AT); Armin Temel, Graz (AT)

(73) Assignee: SEMPERIT AKTIENGESELLSCHAFT HOLDING, Vienna (AT)

( * ) Notice: Subject to any disclaimer, the term of this patent is extended or adjusted under 35 U.S.C. 154(b) by 1869 days.

(21) Appl. No.: 11/530,338

(22) Filed: Sep. 8, 2006

(65) Prior Publication Data

US 2007/0105971 A1    May 10, 2007

(30) Foreign Application Priority Data

Sep. 12, 2005    (AT) .................. A 1491/2005

(51) Int. Cl.
| | | |
|---|---|---|
| B32B 1/02 | (2006.01) | |
| C08J 5/02 | (2006.01) | |
| C08J 3/26 | (2006.01) | |
| C08J 3/28 | (2006.01) | |
| A61B 19/04 | (2006.01) | |
| A61F 6/04 | (2006.01) | |

(52) U.S. Cl.
CPC .... *C08J 5/02* (2013.01); *C08J 3/26* (2013.01); *C08J 3/28* (2013.01); *A61B 19/04* (2013.01); *A61F 6/04* (2013.01); *C08J 2307/02* (2013.01); *C08J 2309/10* (2013.01)

(58) Field of Classification Search
USPC .......................... 264/305, 494, 496
See application file for complete search history.

(56) References Cited

U.S. PATENT DOCUMENTS

| | | | | |
|---|---|---|---|---|
| 3,338,810 A | * | 8/1967 | Warner ........................ 522/33 |
| 3,668,091 A | | 6/1972 | French et al. | |
| 3,816,371 A | | 6/1974 | Baldwin et al. | |
| 3,867,270 A | * | 2/1975 | Malatesta et al. ........... 522/46 |
| 4,186,069 A | | 1/1980 | Muzyczko et al. | |
| 5,691,446 A | * | 11/1997 | Dove ...................... 525/333.7 |
| 6,051,320 A | | 4/2000 | Noecker et al. | |
| 6,254,947 B1 | | 7/2001 | Schaller | |

(Continued)

FOREIGN PATENT DOCUMENTS

| | | |
|---|---|---|
| DE | 2903454 | 8/1979 |
| EP | 0232016 | 8/1987 |

(Continued)

OTHER PUBLICATIONS

Stevens, Malcolm, "Polymer Chemistry" 1999, Oxford university press, Third Edition, p. 266.*

(Continued)

*Primary Examiner* — Galen Hauth
(74) *Attorney, Agent, or Firm* — Greenblum & Bernstein, P.L.C.

(57) ABSTRACT

Method for producing a cross-linked elastomer in which a mixture is produced comprising at least one latex and at least one starter component for initiating the cross-linking reaction or a latex that bears at least one starter component or starter group, in particular in liquid phase. A photoinitiator is used as a starter component, which photoinitiator, through irradiation with electromagnetic radiation in the ultraviolet (UV light) and/or visible spectral range forms a reactive species. The latex mixture is irradiated with UV light and/or visible light.

30 Claims, 1 Drawing Sheet

(56) References Cited

U.S. PATENT DOCUMENTS

| | | | |
|---|---|---|---|
| 6,329,444 | B1 | 12/2001 | McGlothlin et al. |
| 6,383,552 | B1 | 5/2002 | Noecker et al. |
| 6,395,459 | B1 | 5/2002 | Taylor et al. |
| 6,440,498 | B2 | 8/2002 | Schaller |
| 6,803,302 | B2 | 10/2004 | Pozder et al. |
| 6,803,392 | B1 | 10/2004 | Köhler |
| 2004/0049836 | A1* | 3/2004 | Ashraf et al. ............... 2/456 |
| 2004/0071909 | A1 | 4/2004 | McGlothlin et al. |
| 2005/0171282 | A1* | 8/2005 | Park ............................. 525/191 |
| 2006/0253956 | A1* | 11/2006 | Lipinski ........................ 2/168 |

FOREIGN PATENT DOCUMENTS

| | | |
|---|---|---|
| EP | 0486278 | 5/1992 |
| EP | 0856294 | 8/1998 |
| EP | 1193551 | 4/2002 |
| EP | 0792925 | 12/2003 |
| GB | 850523 | 10/1960 |
| GB | 853926 | 11/1960 |
| JP | 51-125482 | 11/1976 |
| JP | 54-91585 | 7/1979 |
| JP | 63-225670 | 9/1988 |
| JP | 6-25450 | 2/1994 |

OTHER PUBLICATIONS

N.B. Cramer & C.N. Bowman, Kinetics of Thiol-Ene and Thiol-Acrylate Photopolymerizations with Real-Time Fourier Transform Infrared, 39 J. Polymer Sci.: Part A: Polymer Chem. 3311 (2001) (citing Posner, 38 Ber. 646 (1905)).*

F. Ashworth & G.N. Burkhardt, Effects Induced by the Phenyl Group. Part I. Addition of Polar Reagents to Styrene and the Behavior of the Halogenated Ethylbenzenes, J. Chem. Soc. 1791, 1797 (1928).*

F.R. Mayo & C. Walling, The Peroxide Effect in the Addition of Reagents to Unsaturated Compounds and in Rearrangement Reactions 27 Chem. Rev.351, 387-394 (1940).*

G.E. Serniuk et al., Study of the Reaction of Buna Rubbers with Aliphatic Mercaptans, 70 J. Am. Chem. Soc. 1804 (1948).*

C.E. Hoyle et al., Thiol-Enes: Chemistry of the Past with Promise for the Future, 42 J. Polymer Sci.: Part A: Polymer Chemistry 5301, 5324-26 (2004).*

C. Decker, Light-Induced Crosslinking Polymerization, 51 Polymer Int'l 1141 (2002).*

C. Decker, Kinetic Study and New Applications of UV Radiation Curing, 23 Macromol. Rapid Communications 1067, 1085-91 (2002).*

C. Decker & T. Nguyen Thi Viet, High-Speed Photocrosslinking of Thermoplastic Styrene-Butadiene Elastomers, 77 J. Applied Polymer Sci. 1902 (2000).*

C. Decker & T. Nguyen Thi Viet, Photocrossl inking of Functionalized Rubbers IX. Thiol-Ene Polymerization of Styrene-Butadiene-Block-Copolymers, 41 Polymer 3905 (2000).*

C. Decker & T. Nguyen Thi Viet, Photocrosslinking of Functionalized Rubbers, 8: The Thiol-Polybutadiene System, 200 Macromol. Chem. Phys. 1965 (1999).*

C. Decker & T. Nguyen Thi Viet, Photocrosslinking of Functionalized Rubbers, 7: Styrene-Butadiene Block Copolymers, 200 Macromol. Chem. Phys. 358 (1999).*

R. Brown et al., The Addition of Thioacetic Acid to Unsaturated Compounds J. Chem. Soc. 2123 (1951).*

V.N. Ipatieff & B.S. Freidman, Reaction of Thiol Compounds with Aliphatic Olefins 61 J. Am. Chem. Soc. 71 (1939).*

English Language Abstract of EP 0 856 294.

English Language Abstract of TW 294 697.

English Language Abstract of JP 63-225670.

Phinyocheep P. et al., "Ultraviolet-curable liquid natural rubber". Journal of Applied Polymer Science, Bd. 78, 2000, pp. 1478-1485.

Tangboriboonrat P. et al., "New Evidence of the Surface Morphology of Deproteinized Natural Rubber Particles", Polymer Bulletin, Springer, Heidelberg, DE, Bd. 41, Nr. 5, Nov. 1998, pp. 601-608, XP000787944, ISSN: 0170-0839.

* cited by examiner

METHOD FOR PRODUCING CROSS-LINKED ELASTOMER

This application claims priority under 35 U.S.C. §119 of Austrian Patent Application No. A 1491/2005, filed on Sep. 12, 2005, the disclosure of which is hereby incorporated by reference thereto in its entirety.

BACKGROUND OF THE INVENTION

1. Field of the Invention

The invention relates to a method for producing a cross-linked elastomer in which a mixture is produced comprising at least one latex and at least one starter component for initiating the cross-linking reaction or a latex that has at least one starter component or starter group in the molecule, in particular in liquid phase, a method for producing a latex product with a predetermined form in which at least one latex is cross-linked and the molding is carried out before or after the cross-linking, a method for producing a dipped article from at least one latex, in particular a glove or a condom, in which a mold in an outer contour that corresponds to the dipped article to be produced is dipped for a predetermined time into a dipping bath containing a mixture with the at least one latex, optionally after dipping in another dipping bath with a coagulating agent, and subsequently the dipped article is solidified and/or dried, optionally after a postcure, a mixture for producing a latex product, comprising at least one latex and at least one starter component for initiating a cross-linking reaction, and optionally further auxiliaries, a mixture for producing a dipped article from at least one latex, in particular a glove or a condom, a glove produced from an elastomer cross-linked with a starter component, formed by elastomer molecules, a device for producing a cross-linked elastomer with a reactor in which a mixture comprising at least one latex and at least one starter component for initiating the cross-linking reaction can be filled, and optionally with at least one circulating device for the mixture, and the use of the mixture according to the invention.

2. Prior Art

In order to give elastomers the specific elastic properties, the polymer chains of the elastomer have to be at least partially cross-linked with one another. The cross-linking generally takes place via double bonds that are either in the main chain, such as, e.g., with polyisoprene, polybutadiene, styrene-butadiene rubber, chloroprene, nitrile-butadiene rubber, or a side chain, such as, e.g., with EPDM, of the elastomer. On an industrial scale the cross-linking of elastomers, including rubber latex, has hitherto been carried out in three different ways.

The most widespread is the cross-linking, i.e., vulcanization, of elastomers by means of molecular sulfur, which dates back to Goodyear. Since vulcanization with sulfur alone entails reaction times that are too long, vulcanization accelerators are added. These are organosulfur compounds, such as dithiocarbamate, mercaptobenzothiazole or xanthogenate. Since the cross-linking of rubber lattices or rubber copolymers has to be carried out at low temperatures so as not to destabilize the latex, the use of very reactive vulcanization accelerators is essential.

Another way of cross-linking elastomers is the reaction with organic peroxides. Compounds, such as dicumyl peroxide or dibenzoyl peroxide, are thereby thermally split into radicals which initiate the cross-linking of the elastomer chains. It is thereby advantageous if work is carried out with the exclusion of air, since peroxides are oxygen-sensitive, which is why the cross-linking is often carried out in molten salt baths.

In addition to the thermal cross-linking methods there are also radiation cross-linking methods in which energetic electron radiation or gamma radiation is used. In these methods additional reagents, such as, e.g., acrylates, are often added to the rubber latex to be cross-linked. A radiation cross-linking method of this type is known, e.g., from U.S. Pat. No. 6,329,444 B. This document describes in particular a medical glove comprising cis-1,4-polyisoprene, whereby this synthetic rubber has the advantage that compared to natural rubber it is protein-free and sulfur-free. This medical glove is made by dip-molding of a prevulcanized cis-1,4-polyisoprene. The prevulcanization or vulcanization is carried out, as mentioned above, by means of electron radiation or gamma radiation without chemical sensitizers. Doses of 20 megarad to 40 megarad are thereby used. Peroxide cross-linking is also described in this US-B1.

Objects and Advantages of the Invention

The object of the present invention is to provide a radiation-chemical cross-linking method for a latex and a latex product produced thereby, which is easier to carry out than conventional known radiation-chemical cross-linking methods.

This object of the invention is attained—in each case independently—in the method according to the invention in that a photoinitiator is used as a starter component, which photoinitiator, through irradiation with electromagnetic radiation in the ultraviolet (UV light) and/or visible spectral range forms a reactive species and the latex mixture is irradiated with UV light and/or visible light, further in the method for producing the latex product or for producing a dipped article from at least one latex in that the cross-linking of the latex is carried out with UV light and/or visible light, with the mixture according to the invention, in which the starter component is a photoinitiator that through irradiation with electromagnetic radiation in the ultraviolet and/or visible spectral range forms a reactive species, and through the mixture for producing a dipped article in which the mixture is composed as described, further through a glove produced according to the method according to the invention in which optionally the starter component and/or decomposition products from the reaction on the elastomer molecules is or are immobilized, and finally independently also through a device in which an energy source is arranged in or on the reactor operatively engaged with the reactor, which device generates the electromagnetic radiation in the ultraviolet and/or visible spectral range.

It is thereby advantageous that through the avoidance of electron or gamma radiation as is used in the prior art to cross-link lattices, the cross-linking method can be designed more simply per se, in particular since no particular expenditures are necessary regarding protection from ionizing radiation, etc. The photochemical cross-linking is less dangerous and can be better regulated. In the mixture according to the invention no conventional sulfur-containing accelerators, such as, e.g., dithiocarbamate or mercaptobenzothiazole are used, whereby the sensitization or skin irritation potential in the use of the latex produced for the medical field is at least reduced. With the mixture according to the invention or the latex articles according to the invention, in particular gloves, no discoloration can be observed when they come into contact with copper surfaces, as is the case with thermally cross-linked mixtures having dithiocarbamate. Through the immobilization of the photoinitiator molecules or the decomposition products forming during photolysis from the photoinitiator molecules on the elastomer molecules, the danger of migration from the finished product is reduced, whereby in turn the danger of sensitization or skin irritation due to the use of these articles is reduced. Moreover, it was established that the latex products produced according to the method according to the invention show a very good aging resistance.

It is possible to use a spectral range for the cross-linking, with wavelengths chosen from a range with a lower limit of 150 nm and an upper limit of 600 nm. This method can thus be used very universally for various types of latex, without the device for carrying out the method having to be specially adapted.

On the other hand it is possible to increase the specificity of the reaction to use a spectral range with wavelengths that are chosen from a range with a lower limit of 250 nm and an upper limit of 475 nm or in another embodiment variant with a lower limit of 275 nm and an upper limit of 400 nm. Secondary reactions that might occur caused by a broad energy spectrum and thus the excitation of other chemical functionalities than those desired, can thus be at least partially prevented. Moreover, it is thus possible to make the method more efficient by choosing highly effective photoinitiators.

In principle, any photoinitiator can be used for the cross-linking method according to the invention which shows a corresponding reaction in the ultraviolet and/or visible spectral range, in particular in the blue range of the visible spectral range adjacent to the UV range. To increase the reaction with suitable reaction engineering, however, starter components are preferred that are chosen from a group comprising compounds that split into radicals under the influence of UV radiation, in particular benzoin derivatives, such as, e.g., (2-carboxyethyl) benzoin methyl ether, benzoin ethyl ether ethoxy-1,2-diphenylethanone, benzoin isopropyl ether propoxy-1,2-diphenylethanone, benzoin isobuthyl ether isobutoxy-1,2-diphenylethanone, mixtures of benzoin n-buthyl ether and benzoin isobutyl ether, methylolbenzoin derivatives, such as, e.g., vinyloxymethylbenzoin methyl ether, 4-benzoyl-1,3-dioxolan derivatives, benzil ketals, such as, e.g., benzil dimethyl ketal, dialkoxyacetophenone, such as, e.g., a,a-diethoxyacetophenone, a,a-di(n-butoxy)acetophenone, hydroxyalkylphenone, such as, e.g., 1-hydroxy-cyclohexyl-phenyl-ketone, 2-hydroxy-2-methyl-1-phenylpropane-1-on, 1-hydroxy-cyclohexyl-phenyl-ketone with 2-hydroxy-2-methyl-1-phenylpropane-1-on, 1-[4-(2-hydroxyethoxy)phenyl]-2-hydroxy-2-methyl-propane-1-on, 1-hydroxy-cyclohexyl-phenyl-ketone with benzophenone, aminoalkylphenones, such as, e.g., 2-methyl-1-[4-(methylthio)phenyl]-2-morpholino-propane-1-on, 2-benzyl-2-dimethylamino-1-(4-morpholinophenyl)-butane-1-on, acylphosphinoxides, such as, e.g., 2,4,6-trimethylbenzoyl-diphenylphosphine oxide, 2,4,6-trimethylbenzoylphenylphosphinic acid ethyl ester, bis(2,4,6-trimethylbenzoyl)-phenylphosphine oxide, o-acyl-a-oximinoketone, peroxides, such as, e.g., dibenzoylperoxide, hydroperoxides, such as, e.g., cumolhydroperoxide, perester, such as, e.g., tert-butyl-perester of aromatic carboxylic acids, alcyloxim ester, ketosulfides, such as, e.g., phenacyl sulfide, disulfides, such as, e.g., dibenzoyidisulfide, dithiocarbamates, such as, e.g., diphenyldithiocarbamate, halogenated acetophenone derivatives, phenylglyoxylates, such as, e.g., methyl a-oxo benzeneacetate, halogen compounds, such as, e.g., alkyl chloride, alkyl bromide, a-halogenketones, such as, e.g., di and trichloroacetophenone, hydrazone, cyclic acetals, such as, e.g., 1,3-dioxalan, sulfur compounds analogous hereto, such as, e.g., 1,3-dithialan, phenylester aliphatic carboxylic acids, and the corresponding anilides, photolabile organic azides, such as, e.g., bis-azidobenzal-cyclohexanon, triphenylsulfonium-hexafluorophosphates, diphenyliodonium tetraflouroborate, disulfones, such as, e.g., diphenyldisulfone, imimosulfonates, thiosulfonates, such as, e.g., S-phenylbenzolthiosulfonate, selenium compounds analogous to the referenced sulfur compounds, such as, e.g., diselenides and mixtures thereof, such as, e.g., at least one benzoin derivative and/or at least one methylolbenzoin derivative and/or at least one 4-benzoyl-1,3-dioxolan derivative and/or at least one benzilketal and/or at least one dialkoxy-acetophenone and/or at least one hydroxyalkylphenone and/or at least one aminoalkylphenone and/or at least one acylphosphine oxide and/or at least one o-acyl-a-oximinoketone and/or at least one peroxide and/or at least one halogenated acetophenone derivative and/or at least one phenylglyoxylate with at least one methylolbenzoin derivative and/or at least one 4-benzoyl-1,3-dioxolane derivative and/or at least one benzilketal and/or at least one dialkoxyacetophenone and/or at least one hydroxyalkylphenone and/or at least one aminoalkylphenone and/or at least one acylphosphine oxide and/or at least one o-acyl-a-oximinoketone and/or at least one peroxide and/or at least one halogenated acetophenone derivative and/or at least one phenylglyoxylate or compounds that under the influence of UV radiation abstract hydrogen with the formation of radicals, in particular benzophenone derivatives, such as, e.g., 2,4,6-trimethyl-benzophenone with benzophenone (80%:20%), 4-chlorobenzophenone, [4-[4-methylphenylthio]-phenyl]-phenylmethanone, 3,3'-dimethyl-4-methoxy benzophenone, methyl-2-benzoylbenzoate, 4-phenyl-benzophenone, 4,4'-bis(dimethylamino)-benzophenone, Michler's ketone, xanthone derivatives, thioxanthone derivatives, such as, e.g., mixtures of 2-chloro- with 4-chloro thioxanthone, 2,4-dimethylthioxanthone, 2,4-diethoxythioxanthone, 1-chloro-4-propoxy-thioxanthone, anthraquinone derivatives, benzyl, diinone compounds, and mixtures thereof, such as, e.g., at least one benzophenone derivative and/or at least one Michler's ketone and/or at least one xanthone derivative and/or at least one thioxanthone derivative and/or at least one anthraquinone derivative and/or benzyl and/or at least one diinone compound with at least one benzophenone derivative and/or at least one Michler's ketone and/or at least one xanthone derivative and/or at least one thioxanthone derivative and/or at least one anthraquinone derivative and/or benzyl and/or at least one diinone compound, or also oligomeric photoinitiators, photoinitiators with vinyl- and/or acryl groups, macromolecules, in particular polymerized or copolymerized photoinitiators, such as, e.g., oligo [2-hydroxy-2-methyl-1-[4-(1-methylvinyl)phenyl]propanone], polymerizable photoinitiators, polymer-bonded photoinitiators, photoinitiators that under irradiation bond to a polymer or rubber matrix, and polymerized vinyl-, allyl-, acryl- or methacryl derivatives of: benzoin derivatives, methylolbenzoin derivatives, 4-benzoyl-1,3-dioxolane derivatives, benzilketals, dialkoxyacetophenones, hydroxy-alkylphenones, aminoalkylphenones, acylphosphine oxides, o-acyl-a-oximinoketones, peroxides, halogenated acetophenone derivatives, phenylglyoxylates, benzophenone derivatives, Michler's ketones, xanthone derivatives, thioxanthone derivatives, anthraquinone derivatives, benzyl, diinone compounds, and mixtures thereof, such as, e.g., at least one oligomeric photoinitiator and/or at least one photoinitiator with vinyl- and/or acryl groups and/or at least one macromolecule, in particular polymerized or copolymerized photoinitiators, such as, e.g., oligo [2-hydroxy-2-methyl-1-[4-(1-methylvinyl)phenyl]propanone] and/or at least one polymerizable photoinitiator and/or at least one polymer-bonded photoinitiator and/or at least one photoinitiator that under irradiation bonds to a polymer or rubber matrix and/or at least one polymerized vinyl-, allyl, acryl- or methacryl derivative of: benzoin derivatives, methylolbenzoin derivatives, 4-benzoyl-1,3-dioxolane derivatives, benzilketones, dialkoxyacetophenones, hydroxyalkyl phenones, aminoalkyl phenones, acylphosphine oxides, o-acyl-a-oximinoketones, peroxides, halogenated acetophenone derivatives, phenylglyoxylates, benzophenone derivatives, Michler's ketones, xanthone derivatives, thioxanthone derivatives, anthraquinone derivatives, benzyl, diinone compounds with at least one oligomeric photoinitiator and/or at least one photoinitiator with vinyl- and/or acryl groups and/or at least one macromolecule, in particular polymerized or copolymerized photoinitiators, such as, e.g., oligo [2-hydroxy-2-methyl-1-[4-(1-methylvinyl)phenyl]propanones] and/or at least one polymerizable photoinitiator and/or at least one polymer-bonded photoinitiator and/or at least one photoinitiator that under irradiation bonds to a polymer or rubber matrix and/or at least one polymerized vinyl-, allyl-, acryl- or methacryl derivative of: benzoin derivatives, methylolbenzoin derivatives, 4-benzoyl-1,3-dioxolane derivatives, benzilketals, dialkoxyacetophenones, hydroxyalkylphenones, aminoalkylphenones, acylphosphine oxides, o-acyl-a-oximinoketones, peroxides, halogenated acetophenone derivatives, phenylglyoxylates, benzophenone derivatives, Michler's ketones, xanthone derivatives, thioxanthone derivatives, anthraquinone derivatives, benzyl, diinone compounds. The individual starter components can be used by themselves individually or in mixtures, whereby also mixtures of at least one compound according to claim 5 and/or at least one compound according to claim 6 and/or at least one compound according to claim 7 with at least one compound according to claim 5 and/or at least one compound according to claim 6, optionally with at least one compound according to claim 8 and/or at least one compound according to claim 7, optionally with at least one compound according to claim 8, are possible without the individual compounds or combinations of compounds being explicitly listed at this point, so as to avoid repetitions.

Alongside or in addition to these starter components, inorganic compounds can also be used as starter components or photocatalysts, such as, e.g., metal oxides, e.g., $ZnO$, $TiO_2$, metal salts and metal complexes, e.g., $FeCl_3$, $ZnCl_2$, $TiCl_4$, $COCl_2$, $MnCl_2$, metal carbonyls, e.g., manganese pentacarbonyl, benzol-chromium-tricarbonyl, dichromate, ferrocene in conjunction with halogen compounds or pseudo-halogen compounds e.g., $CCl_4$ phenylacylthiocyanate, metal complexes, esters of inorganic acids, e.g., tert-butyl nitrite, phenylcyanate, phenylthiocyanate, benzylthiocyanate, phenylacylthiocyanate, acetylacetonates of Co(II), Mn(III), Fe(III), Cu(II).

According to another embodiment variant, it is provided to choose the starter component from a group comprising photoinitiators that can be excited with visible light, in particular titanocene, 1,2-diketones, such as, e.g., benzil, derivatives of acylphosphine oxides, substituted derivatives of stilbene, distyrylbenzol and mixtures thereof, such as, e.g., at least one titanocene and/or at least one 1,2-diketone, such as, e.g., benzil, and/or at least one derivative of acylphosphine oxide and/or at least one substituted derivative of stilbene and/or distyrylbenzol with at least one titanocene and/or at least one 1,2-diketone, such as, e.g., benzil and/or at least one derivative of acylphosphine oxide and/or at least one substituted derivative of stilbene and/or distyrylbenzol.

Mixtures of at least one of the compounds already listed above with at least one compound according to claim 9 are thereby also covered by the extent of the protection.

Moreover, it is possible to increase the reactivity to use the starter components in combination with at least one hydrogen donor, such as, e.g., an amine or thiol.

Preferably, 2,4,6-trimethylbenzoylphenylphosphinic acid ethyl ester and/or 2-hydroxy-2-methyl-1-phenylpropanone is used as a starter component.

For the production of medical latex products, in particular gloves, it is advantageous if for the cross-linking reaction of the latex or the latex mixture with respect to balanced mechanical properties, i.e., in particular a desired strength with corresponding relaxation of the glove, i.e., a reduction of the pressure or the force on the hand after stretching from drawing on the glove, thus avoiding a "constricted feeling" by the wearer or to ensure the corresponding tactile property for the wearer of the glove, if the at least one starter component or a mixture of several starter components is added in a proportion that is chosen from a range with a lower limit of 0.05% by weight and an upper limit of 20% by weight, based on the solids content of the latex in the mixture.

To further improve these effects, it is provided according to the embodiment variant that the at least one starter component or a mixture of several starter components is added in a proportion that is chosen from a range with a lower limit of 0.1% by weight and an upper limit of 10% by weight, based on the solids content of the latex in the mixture or that the at least one starter component or a mixture of several starter components is added in a proportion that is chosen from a range with a lower limit of 0.5% by weight and an upper limit of 4% by weight, in particular 1% by weight or 2% by weight or 3% by weight, based on the solids content of the latex in the mixture.

In order to be able to better form the cross-linking it is advantageous to add at least one cross-linking auxiliary to the mixture. In particular the reaction behavior of the starter component, i.e., of the photoinitiator, can thus be positively influenced.

Preferably at least one thiol, and/or a selenol, such as, e.g., 1,6 hexanediselenol, in particular respectively multifunctional compounds or derivatives thereof, such as, e.g., bisthiols, tristhiols, bisselenols, trisselenols are used as a cross-linking auxiliary, whereby it is provided according to an embodiment variant that the thiol is chosen from a group comprising trimethylolpropane-tris-(3-mercaptopropionate), 1,6-hexane dithiol, and mixtures thereof. The cross-linking speed can be increased by the use of thiols or selenols, in particular multifunctional thiols in that the UV reaction or the reaction in the visible spectral range proceeds at least in part according to the so-called thiol-ene reaction mechanism. Not only is the cross-linking speed influenced thereby, products can also be produced therewith which have higher or better mechanical characteristics, such as, e.g., strength, or also the modulus 500%.

Although they are not explicitly cited in order to avoid repetitions, all the combinations of the listed photoinitiators with at least one of the listed cross-linking auxiliaries are possible and covered by the extent of the protection.

It is thereby advantageous if the cross-linking auxiliary is added in a proportion that is chosen from a range with a lower limit of 0.05% by weight and an upper limit of 20% by weight, based on the solids content of the latex in the mixture, or to further intensify the above-mentioned effects, if the cross-linking auxiliary is added in a proportion that is chosen from a range with a lower limit of 0.1% by weight and an upper limit of 10% by weight, based on the solids content of the latex in the mixture or according to a further embodiment variant according to which it is provided that the cross-linking auxiliary is added in a proportion that is chosen from a range with a lower limit of 0.5% by weight and an upper limit of 4% by weight, based on the solids content of the latex in the mixture.

However, it is also possible to add the cross-linking auxiliary in a proportion that is chosen from a range with a lower limit of 0.5% by weight or 1% by weight and an upper limit of 3% by weight or 1.5% by weight.

At least one further auxiliary can be added to the mixture according to the invention or used in the method according to the invention, chosen from a group comprising, in particular multifunctional, acrylates, such as, e.g., hexane diol diacrylate (HDDA), trimethylolpropane triacrylate (TMPTA), compounds with vinyl or allyl groups, such as, e.g., triallyl cyanurate, triallyl isocyanurate, and mixtures thereof, such as, e.g., at least one listed, in particular multifunctional, acrylate with at least one listed compound with vinyl or allyl groups in order to thus improve the cross-linking behavior, whereby in turn multifunctional compounds are preferred.

This further cross-linking auxiliary is preferably added in a proportion that is chosen from a range with a lower limit of 0.05% by weight and an upper limit of 20% by weight, based on the solids content of the latex in the mixture or according to an embodiment variant to this that is chosen from a range with a lower limit of 0.1% by weight and an upper limit of 10% by weight, based on the solids content of the latex in the mixture or according to a further embodiment variant that is chosen from a range with a lower limit of 0.5% by weight and an upper limit of 4% by weight, in particular 1% by weight or 2% by weight or 3% by weight, based on the solids content of the latex in the mixture.

It is also possible to add at least one sensitizer to the mixture in order to be able to better transmit the light energy to the photoinitiator and to thus accelerate the cross-linking reaction as a whole or to positively influence the process or in order to thus also create the possibility of using photoinitiators that absorb in another absorption region than would be advantageous for the desired reaction.

It is thereby advantageous if this at least one sensitizer is chosen from a group comprising organic colorants such as eosine, inorganic pigments such as zinc-phthalocyanine or titanium oxides, and mixtures thereof, since these compounds, in particular with the photoinitiators used according to the invention, show a corresponding interaction.

The proportion of the sensitizer is preferably in a range with a lower limit of 0.1% and an upper limit of 50% of the proportion of the starter component(s), or in a range with a lower limit of 10% and an upper limit of 40% of the proportion of the starter component(s) or in a range with a lower limit of 15% and an upper limit of 25% of the proportion of the starter component(s), whereby the quantity of sensitizer added is coordinated with the quantity of the photoinitiator used, thus reducing the danger of having unreacted sensitizer molecules in the finished latex product, thus possibly causing a sensitization or skin irritation.

Preferably the at least one starter component and/or the at least one cross-linking auxiliary and/or the at least one sensitizer is pre-emulsified or pre-dispersed to a preliminary emulsion or a predispersion before the addition to the at least one latex and to this end in order to improve the dispersing or emulsifying behavior of these components at least one emulsifying agent or at least one dispersing agent can be added to the mixture according to the invention for the cross-linking method, whereby a surfactant is preferably used as emulsifying agent or dispersing agent, in particular polyethylene glycol sorbitan monolaurate. The introduction of these components into the in particular liquid latex phase is thus facilitated or an "equidistribution" of these components in their total liquid phase can thus be achieved, whereby higher reaction rates, i.e., higher reactions per time unit and thus a shortening of the method can be achieved.

This preliminary emulsion or predispersion can be added to the latex or the latex mixture at least in part before the cross-linking reaction. It is likewise possible to add it at least in part during the cross-linking reaction. It is thus possible to react to the cross-linking reaction, in particular the start of the cross-linking reaction, of different types of latex accordingly, or the use of auxiliary components or starter components can be better adapted to the desired degree of cross-linking. In particular the degree of cross-linking can thereby also be better adapted to the latex or the latex mixture.

The at least one latex to be cross-linked according to the invention can be chosen from a group comprising natural rubber (NR), polyisoprene latex (IR), nitrile-butadiene rubber (NBR), chloroprene latex (CR), styrene-butadiene latex (SBR), lattices of ethyl acrylate copolymers (ACM), lattices of elastomers that are produced by re-emulsification, lattices of functional copolymers, such as, e.g., photoinitiator-containing and/or carboxylated lattices produced from polymer blends, and mixtures thereof, whereby with these lattices— although the use of the method according to the invention for other latex types should not be excluded-surprisingly good mechanical properties or corresponding good properties can be achieved.

It is thereby advantageous if the latex is cross-linked with a solids content that is chosen from a range with a lower limit of 20% and an upper limit of 60%, in particular if the latex is cross-linked with a solids content that is chosen from a range with a lower limit of 30% and an upper limit of 50%, preferably if the latex is cross-linked with a solids content that is chosen from a range with a lower limit of 35% and an upper limit of 45%, since with this solids content a correspondingly good intermixing of the individual educts and thus a quick reaction sequence is possible.

The cross-linking reaction is preferably carried out in a falling-film reactor or in an immersion reactor in order to enable the energy supply if possible to reach into the core areas of the mixture with predetermined layer thicknesses of the reaction mixture.

A mercury lamp and/or a dosed mercury lamp and/or a xenon lamp and/or a pulsed xenon lamp and/or an excimer lamp and/or a laser, such as, e.g., an excimer laser or for the at least proportionate cross-linkings in the visible blue range a laser, an LED light source is preferably used as an energy source for electromagnetic radiation, since a correspondingly high energy yield can be achieved with these light sources or energy sources.

To increase the reaction or to further increase the specificity of the reaction, preferably monochromatic radiation can be used and in particular lasers are used for this.

As already mentioned, the cross-linking method is particularly preferably used for producing a medical glove or a surgical glove. Particularly advantageously a nitrosamine-free glove, in particular of natural rubber, can also be produced herewith.

According to an embodiment variant of the glove according to the invention it is provided that the starter component and/or cleavage products from the reaction is or are covalent-bonded to the elastomer molecules, whereby the effect of a possible migration of the molecules of the starter component or the cleavage products from the glove can be further reduced.

It is likewise possible that at least the one cross-linking auxiliary, in particular a multifunctional thiol, is immobilized, in particular covalent-bonded to elastomer molecules, in order to further minimize the danger of a skin irritation in the use of a glove.

The glove according to the invention can be produced in a nitrosamine-free and/or accelerator-free and/or sulfur-free manner, whereby sulfur-free means that no free sulfur as is used for sulfur cross-linking is present.

According to an embodiment variant of the method according to the invention it is provided that the reactor is flow-connected to a storage vessel for the mixture with the latex, so that only a portion of the latex mixture to be cross-linked thus flows through the reactor and, through the reduction of the layer thickness in the reactor, the conversion rate can thereby be increased.

Finally, at least one dip tank can be arranged downstream of the reactor, i.e., the device according to the invention is part of a production line, in particular for a dip method for producing gloves, whereby the paths between the individual reactors can be shortened and thus the production time as a whole can be likewise shortened.

BRIEF DESCRIPTION OF THE FIGURES

For a better understanding of the invention, it is also explained in more detail based on the following figures.

They show, respectively in a greatly simplified diagrammatic representation.

DETAILED DESCRIPTION OF PREFERRED EMBODIMENTS

It should be noted that in the embodiments variably described the same parts are provided with the same reference numbers or the same component names, whereby the disclosures contained in the specification as a whole can be transferred analogously to the same parts with the same reference numbers or the same component names. The positional references chosen in the specification, such as, e.g., above, below, at the side, etc., refer to the figure directly described and shown and in the case of a change of position are to be transferred to the new position analogously. Furthermore individual features or combinations of features from the different exemplary embodiments shown and described can represent independent inventive solutions or solutions according to the invention.

All the data on ranges in the present specification should be understood to include any and all partial ranges thereof, e.g., the specification 1 to 10 should be understood to mean that all partial ranges, based on the lower limit 1 and the upper limit 10 are included, i.e., all the partial ranges beginning with a lower limit of 1 or more and ending with an upper limit of 10 or less, e.g., 1 to 1.7 or 3.2 to 8.1 or 5.5 to 10.

It should be pointed out here that according to the invention a latex that bears the functional group, i.e., that group on which the starter component for the photolysis is based, on the elastomer molecule is also cross-linked. To simplify matters, these groups were or are not cited separately in the specification, since they are self-explanatory anyway to one skilled in the art based on the teaching regarding the starter components.

Figure 1:
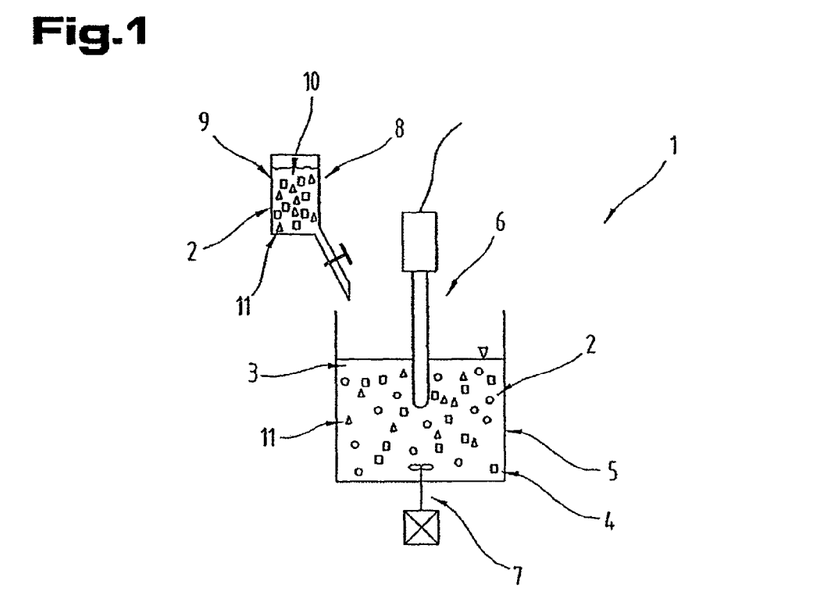
FIG. 1 A first embodiment variant of the device according to the invention.

FIG. 1 shows a device 1 for the cross-linking of a latex 2 or a latex mixture (shown by circles in FIG. 1). The latex 2 is thereby a constituent of a mixture 3 which, in addition to the latex 2, contains at least one starter component 4 (shown by squares) in the form of a photoinitiator. The starter component 4 can also be formed by a mixture 3 of various starter components 4.

This mixture 3 is contained in a reactor 5 the device 1, whereby with the present embodiment of the device 1 the reactor 5 is embodied as an immersion reactor.

An energy source 6 in the form of a light source is immersed in the mixture 3 of the reactor 5. This energy source 6 is designed to emit electromagnetic radiation in the ultraviolet spectral range. This energy source 6 can optionally also be designed to emit electromagnetic waves from the visible range, in particular the blue range of the visible spectrum. Combinations of the UV range with the visible range, in particular with the blue range of the spectrum adjacent to the UV range are also possible.

With the aid of this energy source 6, energy in the form of photons is transferred to the starter component 4, i.e., its molecules, and a radical splitting of the molecules of the starter component 4 can thus be initiated. With the aid of the radicals thereby forming, double bonds that are present in the latex molecules, e.g., in the main chain and/or in a side chain, can be subsequently broken up according to the radical reaction mechanism and the cross-linking can thus take place via starter molecules or directly between the elastomer molecules. The energy source 6 is thereby preferably formed by one of the energy sources already mentioned above, e.g., a mercury lamp or by a laser.

To homogenize the mixture 3 in the reactor 5, an agitator 7 or a corresponding device with comparable function can be arranged therein, as indicated in FIG. 1.

Furthermore, there is a possibility of arranging a storage vessel 8 adjacent to the reactor 5, in which storage vessel the starter component 4 is provided in a preliminary emulsion or predispersion optionally with a corresponding emulsifying agent 10 according to an embodiment variant of the invention. For example, surfactants, as already mentioned, can be used as an emulsifying agent 10.

Moreover, according to another embodiment variant there is a possibility of adding at least one auxiliary to the mixture 3 and/or preliminary emulsion 9. This auxiliary can be, e.g., a cross-linking auxiliary 11—shown by a triangular shape in FIG. 1. For example there is the possibility of providing a thiol and/or a selenol as a cross-linking auxiliary. The thiol preferably has two or more SH groups, whereby the possibility of the so-called thiol-ene addition reaction is available in order to thus create cross-link points in the polymer. An acceleration of the cross-linking reaction can thus be carried out. In addition to this cross-linking auxiliary 11, other cross-linking auxiliaries or other supplementary agents, such as, e.g., sensitizers, hydrogen donors, various process additives, such as, e.g., stabilizers, antifoamants, dispersants, emulsifiers, coagulants, cross-linking chemicals, colorants as well as fillers can also be present in the mixture 3 or at least partially present in the preliminary emulsion 9, whereby these reagents are at least mainly known from the prior art and one skilled in the art is referred at this point to the relevant literature in this regard, e.g., the applicant's EP 0 856 294 A1 or to publication "Kautschuktechnologie" (Rothemeyer/Sommer, Carl Hanser Verlag 2001).

The preliminary emulsion or predispersion can be added at least in part to the mixture 3 before the start of the cross-linking reaction or the pre-cross-linking reaction in the event that a possible post-cross-linking of latex products produced should take place. It is likewise possible to add them at least partially during the reaction of this mixture 3, e.g., to add them in small amounts, e.g., to add them drop by drop.

The energy source can emit light in the spectral range already described, thus in particular between 200 nm and 550 nm or 250 nm and 475 nm or 275 nm and 400 nm.

With regard to the starter component or possible mixtures of different starter components, reference is made at this point to the above forms.

The energy source 6 and the agitator 7 or optionally further components of the device 1 can be operatively engaged with a control or regulating device (not shown), such as, e.g., a PC or in general a data processing device, so that optionally an automation or a process sequence with variable reaction parameters can be carried out in a fully automatic manner. In order to, e.g., change the temperature, a corresponding heating and/or cooling device from the prior art can be arranged on or in the reactor 5.

Furthermore, it is possible to carry out the cross-linking or the pre-cross-linking at a pressure that is different to the atmospheric pressure, e.g., with a vacuum, it is likewise possible to carry out the cross-linking reaction with excess pressure and the reactor 5 can be embodied accordingly in this respect, thus, e.g., vacuum-tight, whereby all inlets or lead-throughs through the walls of the reactor 5 should also be embodied in a vacuum-tight manner or also to be suitable for carrying out excess-pressure reactions, thus, e.g., with reinforced walls.

Figure 2:
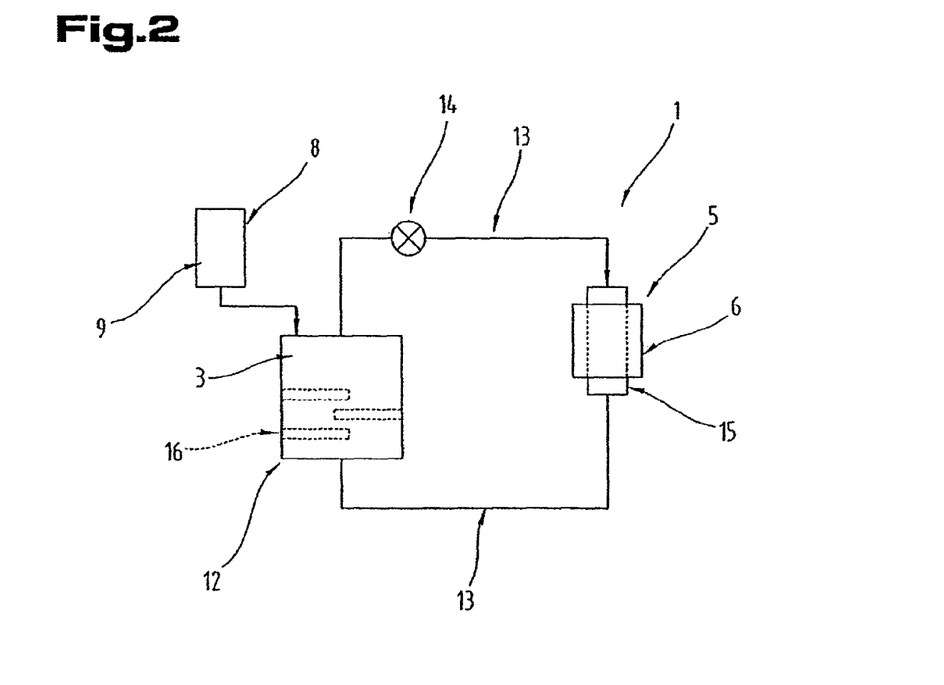
FIG. 2 Another embodiment variant of the device according to the invention.

In addition to the "immersion reactor" embodiment variant, as shown in FIG. 1, according to the invention there is, i.a., also the possibility of embodying the reactor 5 as a falling-film reactor, as shown in FIG. 2. In this embodiment variant of the device 1, in addition to the reactor 5 it also comprises facultatively a storage vessel 12 that is flow-connected to the reactor 5 via a pipe 13, whereby the pipe 13 together with a circulation device 14, e.g., a pump, and the reactor 5 and the storage device 12 in which the mixture 3 is provided forms a circuit through which the mixture 3 is conveyed by the effect of the circulation device 14.

On at least one surface 15, the falling-film reactor 5 has the energy source 6, thus, e.g., again a mercury lamp or a laser, whereby corresponding provisions, such as, e.g., windows, can be provided in the surface 15, in order to make it possible for the electromagnetic radiation to penetrate into the interior of the reactor 5. Furthermore, it is possible to make this reactor 5 at least in part from a transparent material, such as, e.g., (quartz) glass or plastic.

However, the arrangement of the energy source can also be carried out in the interior of the falling film reactor 5, so that the mixture 3 is thus irradiated from the inside outwards, With this embodiment variant there is also the possibility of arranging the storage vessel 8 in an operatively engaged manner with the storage vessel 12 for the mixture 3 and to feed the preliminary emulsion 9 or the predispersion from this storage vessel 8 in the storage vessel 12. Of course, there is also the possibility here of providing a preliminary emulsion directly in this storage vessel 12 for the mixture 3.

As shown by shading in FIG. 2, there is the possibility of providing deflection installations 16, e.g., deflector plates that can optionally have perforations, in the interior of the storage vessel 12, in order to achieve a forced flow in the storage vessel 12, in order to thus effect an intermixing of the mixture 3, so that the agitator 7 according to FIG. 1 can optionally be omitted.

In general, it can be stated that the reactor 5 and/or the storage vessel 8 or the storage vessel 12 can be part of a production line for a production of latex products, e.g., gloves, in particular medical examination gloves or surgical gloves. These are usually produced in a dipping method, whereby it is noted that the invention is not limited to dipped articles per se, but latex products can be produced per se according to the invention by cross-linking of the latex or the lattices in the claimed spectral range.

Dipping methods for gloves are known per se from the prior art and one skilled in the art is referred, e.g., to EP 0 856 294 A, in particular FIGS. 4 and 5 of this EP-A and the relevant statements in column 14, line 38 through column 18, line 51, in particular with respect to the statements regarding coagulation, dipping in latex, various washing operations, various aftertreatments, such as, e.g., chloridizing or halogenating the surface of the gloves or of the latex, the production of surface roughness or the provision of powder-free gloves, etc. This is to avoid unnecessary repetitions of the prior art in connection with the present invention, and EP 0 856 294 A1 therefore forms part of the disclosure of the present invention at least to the aforesaid extent.

Of course, it is possible for the pre-cross-linking or cross-linking of the latex or the lattices to be carried out separately, i.e., independently of the rest of the production unit for latex products.

In addition to gloves, other latex products can also be produced according to the invention, such as, e.g., condoms, various medical latex products, such as, e.g., catheters, diaphragms, infusion bags, medical tubing, tissue culture vessels, etc., or also latex products from the consumer goods sector, such as, e.g., water wings, pacifiers, etc.

To avoid unnecessary repetition, in general reference is made at this point to above statements regarding the photo-initiators used, the various auxiliaries and their concentrations or proportions in the mixture 3, as well as for the applicable latices and their proportion in the mixture 2.

Within the scope of the invention, solids used can be dissolved in a solvent and/or emulsified in water.

It is furthermore possible within the scope of the invention to carry out an aftertreatment, e.g., by heating, irradiating or extracting, after the molding.

The tearing strength of the latex films produced within the scope of the invention can be in the range of 25 N/mm$^2$ for natural rubber with a breaking elongation of 800%-900%.

It is further possible to carry out the radiation-chemical cross-linking continuously as well as discontinuously.

A few examples are given below that have been carried out within the scope of the invention.

EXAMPLE 1

1800 g high ammonia natural rubber (NR) latex with 40% solids content is added to 1 phr (parts per hundred parts of rubber, based on the dry rubber) trimethylopropane tris(3-mercaptopropionate) (as 50% emulsion in water with 5% polyethylene glycolsorbitan monolaurate ("Tween 20") as emulsifier) and 1.5 phr oligo [2-hydroxy-2-methyl-1-[4-(1-methylvinyl)phenyl]propanone] (Esacure KIP-150, Lamberti spa, as 25% solution in iso-propanol) and agitated for 2 hours by means of a magnetic agitator. Subsequently, 200 mL of this latex mixture is placed in a storage vessel and pumped by means of a peristaltic pump with a conveying capacity of approx. 250 mL/min in circulation through a UV flow reactor. The UV flow reactor comprises a cylindrical vessel that is made of brass and is provided on the inside with a chromium layer. The interior diameter is 45 mm. A UV immersion lamp with cooler is placed in this vessel, whereby the distance between the surface of the cooler and the interior wall of the reactor is 1 mm. The reaction product (i.e., the latex mixture) is added in the lower part of the reactor and in the upper part it is drawn off again. The UV flow reactor is equipped with a TQ-150 UV radiator (150 watt, unfiltered, manufactured by Heraeus, Germany) with quartz glass cooler. The latex mixture is pumped through the UV flow reactor in circulation for 30 minutes until as a result of the UV irradiation the desired degree of cross-linking has been achieved. The reaction temperature is 20° C.

The UV-cross-linked latex is removed from the reactor. With the aid of a blade, latex films with 125 micrometer wet film thickness are spread onto zinc oxide paper and dried in air for 120 minutes at 20° C. Disks (diameter 25 mm) are produced from these latex films with a stamping tool and placed in toluene until the equilibrium swelling has been reached. The degree of swelling (in %) can be determined from the increase of the diameter of the disk. In this case it is approx. 80%.

Films are produced from the UV-cross-linked NR latex in an industrially conventional coagulation dipping method. A cylindrical porcelain mold is first dipped in the solution of a coagulant (10% by weight $CaCl_2$ in water), after 60 sec drying at 120° C. dipped in the UV-cross-linked latex (30 sec) and subsequently dried for 20 minutes at 120° C. After cooling to room temperature has been completed, the latex film is removed from the porcelain mold. The film thickness is typically 250 μm. In a tensile test (according to ASTM standard D412-98a), these films had a tearing strength between 25 and 27 $N/mm^2$ and a breaking elongation between 850 and 1000%.

EXAMPLE 2

450 g high ammonia natural rubber (NR) latex with 40% solids content is added to 2 phr 2,4,6-trimethylbenzoylphenylphosphinic acid ethylester (Lucirin TPO-L, BASF, as 50% emulsion in water with 5% polyethyleneglycol-sorbitan-monolaurate ("Tween 20") as emulsifier) and agitated for 2 hours by means of a magnetic agitator. Subsequently, 200 mL of this latex mixture is placed in a storage vessel and pumped by means of a peristaltic pump with a conveying capacity of approx. 250 mL/min in circulation through the UV flow reactor described above (see example 1).

To determine the degree of swelling, test pieces are produced according to the method described in example 1.

According to the equilibrium swelling method described above, the following degrees of cross-linking are determined for the UV-cross-linked NR latex as a function of the UV irradiation time (see table 1):

TABLE 1

| | UV-cross-linking time [min.] | | | | | |
|---|---|---|---|---|---|---|
| | 5 | 10 | 15 | 20 | 25 | 30 |
| Degree of swelling (maturity level) [in %] | 142 | 120 | 114 | 106 | 104 | 100 |

EXAMPLE 3

Synthetic polyisoprene (IR) latex (Kraton IR-401, obtained from KRATON) is stabilized with 1 phr Nekal BX (obtained from BASF, Germany) and diluted to 40% solids content. 0.5 phr trimethylolpropane tris(3-mercaptopropionate) (as 50% emulsion in water with 5% polyethylene glycol-sorbitan-monolaurate ("Tween 20") as emulsifier) and 0.5 phr 2-hydroxy-2-methyl-1-phenylpropanone (Darocure 1173, Ciba Specialty Chemicals, as 50% emulsion in water with 5% polyethylene glycol-sorbitan-monolaurate ("Tween 20") as emulsifier) is added to the stabilized polyisoprene latex and agitated for 2 hours by means of a magnetic agitator. Subsequently 200 mL of this latex mixture are placed in a storage vessel and pumped by means of a peristaltic pump with a conveying capacity of approx. 250 mL/min in circulation through the UV flow reactor described above (see example 1).

To determine the degree of swelling, test pieces are produced according to the method described in example 1.

According to the equilibrium swelling method described above, the following degrees of cross-linking are determined for the UV-cross-linked IR latex as a function of the UV irradiation time (see table 2):

TABLE 2

| | Cross-linking time [min.] | | | | | |
|---|---|---|---|---|---|---|
| | 5 | 7 | 9 | 11 | 13 | 15 |
| Degree of swelling (maturity level) [in %] | 120 | 108 | 102 | 96 | 92 | 92 |

The exemplary embodiments show possible embodiment variants of the invention, whereby it is noted at this point that the invention is not restricted to the embodiment variants specially shown, but rather diverse combinations of the individual embodiment variants among one another are possible, and this variation possibility lies in the ability of one skilled in the art active in this technical field based on the teaching for technical practice through the present invention. Therefore all the conceivable embodiment variants that are possible by combining individual details of the embodiment variant shown and described are also covered by the scope of protection.

For the sake of order, in conclusion it is noted that in order to better understand the structure of device 1, this device or its components were shown in part not to scale and/or enlarged and/or reduced.

The object on which the independent inventive solutions are based can be taken from the specification.

Above all, the individual embodiments shown in FIGS. 1; 2 can form the subject matter of independent inventive solutions. The relevant inventive objects and solutions can be taken from the detailed descriptions of these figures.

The invention claimed is:

1. Method for producing a cross-linked elastomer comprising:
   producing a mixture of at least one latex and at least one starter component for initiating a cross-linking reaction or at least one latex that bears at least one starter component or starter group, the starter component or starter group comprising at least one photoinitiator which through irradiation with electromagnetic radiation in the ultraviolet and/or visible spectral range forms a reactive species, and the mixture includes at least one cross-linking auxiliary comprising at least one of a thiol and a selenol; and
   irradiating the mixture with UV light and/or visible light to at least partially cross-link the at least one latex.

2. The method according to claim 1, wherein the electromagnetic radiation includes wavelengths selected from a range with a lower limit of 150 nm and an upper limit of 600 nm.

3. The method according to claim 1, wherein the electromagnetic radiation includes wavelengths chosen from a range with a lower limit of 275 nm and an upper limit of 400 nm.

4. The method according to claim 1, wherein at least one of the at least one starter component and/or the at least one cross-linking auxiliary and/or at least one sensitizer is or are pre-emulsified or pre-dispersed to a preliminary emulsion or a predispersion before adding the at least one latex to the mixture.

5. The method according to claim 4, wherein at least one emulsifier or dispersion agent is added to the preliminary emulsion or predispersion.

6. The method according to claim 5, wherein the preliminary emulsion or predispersion is added to the latex at least in part before the cross-linking of the at least one latex.

7. The method according to claim 5, wherein the preliminary emulsion or predispersion is added to the latex at least in part during the cross-linking of the at least one latex.

8. The method according to claim 1, wherein the electromagnetic radiation is monochromatic radiation.

9. A method for producing a latex product with a predetermined form, comprising at least partially cross-linking at least one latex by irradiating a mixture with UV light and/or visible light to at least partially cross-link the at least one latex, the mixture comprising at least one latex and at least one starter component for initiating the cross-linking reaction or at least one latex that bears at least one starter component or starter group, the starter component or starter group comprising at least one photoinitiator which through irradiation with electromagnetic radiation in the ultraviolet and/or visible spectral range forms a reactive species, and the mixture includes at least one cross-linking auxiliary comprising at least one of a thiol and a selenol; and molding the least one latex before or after the at least partial cross-linking.

10. Method for producing a dipped article from at least one latex, comprising dipping for a predetermined time a mold with an outer contour that corresponds to the dipped article to be produced in an dipping bath containing a mixture including the at least one latex, and subsequently hardening and/or drying the dipped article, the at least one latex is cross-linked before or after the dipping by the method according to claim 1.

11. The method according to claim 1, wherein the mixture of at least one latex and at least one starter component for initiating the cross-linking reaction or at least one latex that bears at least one starter component or starter group is in liquid phase.

12. The method according to claim 9, wherein a post-cross-linking is performed after the molding.

13. The method according to claim 10, wherein the article comprises a glove or a condom.

14. The method according to claim 10, further including dipping in another dipping bath including a coagulant.

15. The method according to claim 1, wherein the at least one of a thiol and a selenol comprises a multifunctional compound or a derivative thereof.

16. The method according to claim 1, wherein the at least one of a thiol and a selenol comprises at least one of a bisthiol, a tristhiol, a bisselenol and a trisselenol.

17. The method according to claim 1, wherein the at least one of a thiol and a selenol comprises at least one thiol, and the at least one thiol comprises trimethylolpropane-tris-(3-mercaptopropionate), or 1,6-hexane dithiol, or mixtures thereof.

18. The method according to claim 9, wherein the at least one of a thiol and a selenol comprises a multifunctional compound or a derivative thereof.

19. The method according to claim 9, wherein the at least one of a thiol and a selenol comprises at least one of a bisthiol, a tristhiol, a bisselenol and a trisselenol.

20. The method according to claim 9, wherein the at least one of a thiol and a selenol comprises at least one thiol, and the at least one thiol comprises trimethylolpropane-tris-(3-mercaptopropionate), or 1,6-hexane dithiol, or mixtures thereof.

21. The method according to claim 1, further comprising including at least one sensitizer in the mixture in order to better transmit the electromagnetic energy in the ultraviolet and/or visible spectral range to the at least one photoinitiator.

22. The method according to claim 21, wherein the at least one sensitizer is chosen from organic colorants, inorganic pigments, and mixtures thereof.

23. The method according to claim 21, wherein the at least one sensitizer is included in a proportion that is chosen from a range with a lower limit of 0.1% and an upper limit of 50% of the proportion of the at least one starter component.

24. The method according to claim 1, wherein the at least one latex comprises natural rubber, nitrile-butadiene rubber, chloroprene latex, styrene-butadiene latex, lattices of ethyl acrylate copolymers, lattices of elastomers that are produced by re-emulsification, lattices of functional copolymers, or lattices produced from polymer blends, or mixtures thereof.

25. The method according to claim 9, further comprising including at least one sensitizer in the mixture in order to better transmit the electromagnetic energy in the ultraviolet and/or visible spectral range to the at least one photoinitiator.

26. The method according to claim 25, wherein the at least one sensitizer is chosen from organic colorants, inorganic pigments, and mixtures thereof.

27. The method according to claim 25, wherein the at least one sensitizer is included in a proportion that is chosen from a range with a lower limit of 0.1% and an upper limit of 50% of the proportion of the at least one starter component.

28. The method according to claim 9, wherein the at least one latex comprises natural rubber, nitrile-butadiene rubber, chloroprene latex, styrene-butadiene latex, lattices of ethyl acrylate copolymers, lattices of elastomers that are produced by re-emulsification, lattices of functional copolymers, or lattices produced from polymer blends, or mixtures thereof.

29. The method according to claim 13, wherein the glove is nitrosamine-free.

30. The method according to claim 10, wherein the article comprises a glove.

* * * * *